United States Patent
Paul et al.

(10) Patent No.: US 9,676,705 B2
(45) Date of Patent: Jun. 13, 2017

(54) PROCESS FOR THE PRODUCTION OF NITRILES USING A CATALYST BASED ON ANTIMONY AND IRON

(71) Applicants: ECOLE CENTRALE DE LILLE, Villeneuve D'Ascq (FR); UNIVERSITE DES SCIENCES ET TECHNOLOGIES DE LILLE—LILLE 1, Villeneuve D'Ascq (FR)

(72) Inventors: Sebastien Paul, Thun Saint Amand (FR); Benjamin Katryniok, Meurchin (FR); Franck Dumeignil, Fretin (FR); Carsten Liebig, Worms (DE); Wolfgang Holderich, Franckenthal (DE); Cyrille Guillon, Lille (FR)

(73) Assignees: ECOLE CENTRALE DE LILLE, Villeneuve d'Ascq (FR); UNIVERSITE DES SCIENCES ET TECHNOLOGIES D, Villeneuve d'Ascq (FR)

( * ) Notice: Subject to any disclaimer, the term of this patent is extended or adjusted under 35 U.S.C. 154(b) by 0 days.

(21) Appl. No.: 14/774,783

(22) PCT Filed: Apr. 16, 2014

(86) PCT No.: PCT/FR2014/050924
§ 371 (c)(1),
(2) Date: Sep. 11, 2015

(87) PCT Pub. No.: WO2014/170604
PCT Pub. Date: Oct. 23, 2014

(65) Prior Publication Data
US 2016/0023995 A1 Jan. 28, 2016

(30) Foreign Application Priority Data
Apr. 17, 2013 (FR) ...................................... 13 53478

(51) Int. Cl.
*C07C 253/26* (2006.01)
*B01J 23/843* (2006.01)

(52) U.S. Cl.
CPC ......... *C07C 253/26* (2013.01); *B01J 23/8435* (2013.01); *Y02P 20/52* (2015.11)

(58) Field of Classification Search
CPC ... C07C 253/26; C07C 255/08; B01J 23/8435
USPC ........................ 558/316, 318, 319, 320, 325
See application file for complete search history.

(56) References Cited

U.S. PATENT DOCUMENTS 3,197,419 A * 7/1965 Gertisser .............. B01J 23/8435
502/249

FOREIGN PATENT DOCUMENTS

GB 2302291 * 6/1995
WO 2009063120 5/2009

OTHER PUBLICATIONS

"Glycerol conversion to acrylonitrile by consecutive dehydration over WO3/TiO2 and ammoxidation over Sb—(Fe,V)—O" Applied Catalysis G: Environmental, 132-133, p. 170-182, 2013 (available online Nov. 30, 2012).*
"Indirect Ammoxidation of Glycerol into Acrylonitrile via the Intermediate Acrolein" Aachen, Techn. Hochsch., Diss., Oct. 10, 2012, p. 1-173.*
Burrington ("Aspects of selective oxidation and ammoxidation mechanisms over bismuth molybdate catalysts III. Allyl alcohol as a probe for the allylic intermediate" 63, 1980, p. 235-254).*
Cathala ("Ammoxydation catalytique des hydrocarbures et reactions apparentees XXI. Essais d'ammoxydation d'aldehydes, cetones et alcools" Bulletin de la Societe chimique de France, 5-6, 1979, p. 173-178).*
"Two-dimensional oxide catalysts: propene oxidation on FeSb04" Catalysis Letters dated 1995.
Search Report dated 2013.

\* cited by examiner

*Primary Examiner* — Jafar Parsa
*Assistant Examiner* — Amy C Bonaparte
(74) *Attorney, Agent, or Firm* — Ipsilon USA, LLP

(57) ABSTRACT

A compound of the formula $Sb_xFe_1O_y$ (I) in which x varies from 0.4 to 1 inclusive and y varies from 1.6 to 4 inclusive, may be used as a catalyst for catalyzing the ammoxidation reaction of an alcohol of following formula (II) $CH_2{=}C(R^1){-}CH_2{-}OH$ (II) in which $R^1$ represents a hydrogen atom or a methyl radical, to give nitrile of following formula (III) $CH_2{=}C(R^1){-}C{\equiv}N$ (III) in which $R^1$ has the same meaning as in above formula (II), the said reaction being carried out in the gas phase, the said gas phase comprising at least oxygen and ammonia. The present invention also relates to the process for the ammoxidation of an alcohol of formula (II) employing a compound of formula (I) as catalyst.

10 Claims, No Drawings

PROCESS FOR THE PRODUCTION OF NITRILES USING A CATALYST BASED ON ANTIMONY AND IRON

RELATED APPLICATIONS

This application is a National Phase Application of PCT/FR2014/050924, filed on Apr. 16, 2014, which in turn claims the benefit of priority from French Patent Application No. 13 53478 filed on Apr. 17, 2013, the entirety of which are incorporated herein by reference.

BACKGROUND

Field of the Invention

The present invention relates to the use of a catalyst based on antimony and iron to catalyse the production of nitriles, in particular of acrylonitrile, and also to a process for the production of nitriles, in particular acrylonitrile, in the gas phase, in the presence of such a catalyst.

Description of Related Art

Propenenitrile ($CH_2$=CH—C≡N), more commonly known as acrylonitrile, is a starting material which can be used as monomer in the preparation of many polymers in organic chemistry, in particular textile fibres, such as acrylic fibres, nylon or of synthetic rubber or else of nitrogen-comprising elastomers, after copolymerization with butadiene, or else again of high performance solid resins (acrylonitrile/butadiene/styrene (ABS) resins), after copolymerization with butadiene and styrene.

The industrial production of acrylonitrile is today dependent on propene or propane, which are both compounds resulting from fossil resources. Specifically, the synthesis of acrylonitrile is usually carried out according to the "Sohio" process (from the name of the company Standard Oil of Ohio), developed in the 1960s and as described, for example, in Patent Application GB 709 337. This process consists in carrying out the oxidation of propene in the presence of ammonia (ammoxidation) according to the following reaction:

This reaction is carried out in the gas phase in a fluidized bed reactor, at high temperature, generally at 350-400° C., in the absence of water and in the presence of a catalyst based on bismuth and molybdenum.

However, this process exhibits the disadvantage of employing propene, the cost price of which is always increasing.

OBJECTS AND SUMMARY

A need thus exists for a process for the preparation of acrylonitrile which is independent of propene while resulting in excellent yields. The inventors set themselves in particular the aim of developing a process which makes it possible to produce acrylonitrile from allyl alcohol. Furthermore, the latter can be biosourced, which contributes an environmental advantage to such a process, even if the latter did not prove, in fine, economic. It was during these research studies that the inventors discovered that the use of a specific catalyst based on antimony and iron makes it possible in particular to catalyse the reaction for the production of acrylonitrile from allyl alcohol in the gas phase with a very good yield.

A first subject-matter of the present invention is thus the use of a compound of following formula (I):

in which x varies from 0.4 to 1 inclusive and y varies from 1.6 to 4 inclusive, as catalyst for catalysing the ammoxidation reaction of an alcohol of following formula (II) $CH_2$=C($R^1$)—$CH_2$—OH (II), in which $R^1$ represents a hydrogen atom or a methyl radical, to give a nitrile of following formula (III) $CH_2$=C($R^1$)—C≡N (III), in which $R^1$ has the same meaning as in the above formula (II), the said reaction being carried out in the gas phase, the said gas phase comprising at least oxygen and ammonia.

The use of the catalyst of formula (I) above makes it possible to carry out the ammoxidation reaction of an alcohol of formula (II) to result in a nitrile of formula (III), corresponding in particular to acrylonitrile, in the gas phase, with a very good yield. This reaction also makes it possible to access, as byproducts, acrolein (and acrylic acid, by subsequent oxidation of the acrolein), acetone, acetaldehyde, acetonitrile and propionaldehyde, which can also be enhanced in value as they are intermediates widely used in the chemical industry. Furthermore, in the light of the different boiling points of each of these products (acetaldehyde: 22° C.; propionaldehyde: 47° C.; acrolein: 52° C.; acetone: 57° C.; acrylonitrile: 77° C., acetonitrile: 82° C.; acrylic acid: 147° C.), their separation is theoretically easy to carry out, for example even within a dedicated integrated process.

Furthermore, as mentioned above, the starting material (the alcohol of formula (II)) can be produced from renewable resources, which makes it possible to dispense with fossil resources in order to access the nitriles of formula (III) and in particular acrylonitrile. For example, glycerol, alone or as a mixture with formic acid, can be used to produce allyl alcohol according to various catalytic processes in the gas phase or in the liquid phase described in the literature, in particular in International Applications WO 2008/092115 and WO 2011/08509.

By way of example, the catalyst of formula (I) above can in particular be prepared according to the process described by Li K.-T. et al. (Applied Catalysis A: General, 156, 1997, 117-130). Briefly, this process consists in reacting an aqueous acidic solution of an iron salt, such as, for example, iron nitrate, at a temperature of approximately 80° C., with antimony oxide ($Sb_2O_3$) and in then maintaining the temperature between 80 and 90° C. for several hours, in order to evaporate the solvent and to obtain a pasty product which is subsequently dried at approximately 100° C. for several days. The catalyst powder obtained is subsequently pressed in the form of pellets which are subsequently ground to give a powder which is preferably calcined under static air for at least 30 min at a temperature preferably of between 300 and 700° C.

Another subject-matter of the present invention is a process for the production of a nitrile from an alcohol in the presence of a catalyst, characterized in that it comprises a stage of ammoxidation of an alcohol of following formula (II):

in which $R^1$ represents a hydrogen atom or a methyl radical, to result in a nitrile of following formula (III):

$$CH_2=C(R^1)-C\equiv N \quad (III)$$

in which $R^1$ has the same meaning as in the above formula (II), the said reaction being carried out in the gas phase, the said gas phase comprising at least ammonia and oxygen, and in the presence of a solid catalyst chosen from the compounds of following formula (I):

$$Sb_xFe_1O_y \quad (I)$$

in which x varies from 0.4 to 1 inclusive and y varies from 1.6 to 4 inclusive.

The process in accordance with the invention might make it possible to do without fossil resources in the case where the starting materials (alcohols of formula (II) and in particular allyl alcohol) result from biomass. It is simple to carry out (just one stage) and very selective. It results in the nitriles of formula (III), in particular in acrylonitrile ($R^1$=H), with yields of greater than 80%. The separation of the coproducts of the reaction can be carried out according to techniques known to a person skilled in the art and these coproducts can also be enhanced in value as they are advantageous intermediates in the chemical industry.

When $R^1$ represents a hydrogen atom, then the alcohol of formula (II) is allyl alcohol and the nitrile of formula (III) is acrylonitrile.

When $R^1$ represents a methyl radical, then the alcohol of formula (II) is methallyl alcohol and the nitrile of formula (III) is methacrylonitrile.

According to a preferred embodiment of the invention, $R^1$ represents a hydrogen atom. Thus, according to this preferred embodiment, the process in accordance with the invention comprises a stage of ammoxidation of allyl alcohol to give acrylonitrile.

The catalyst is preferably chosen from the compounds of formula (I) in which x varies from 0.5 to 0.8 inclusive. A catalyst of formula (I) which is particularly preferred according to the invention is chosen from the compounds in which x=0.6.

The ammoxidation reaction is preferably carried out at a temperature of greater than or equal to approximately 400° C. and more preferably still at a temperature varying inclusively from 350 to 450° C. approximately.

According to a preferred embodiment of the process in accordance with the invention, the ammoxidation reaction is carried out at atmospheric pressure.

The contact time, defined as being the ratio of the volume of catalyst (in ml) to the total flow rate by volume of gas injected into the reactor (in ml/s), calculated at the temperature and at the pressure of the reaction, preferably varies from 0.05 to 2 s approximately and more preferably still from 0.05 to 0.5 s approximately.

Within the gas phase, the alcohol of formula (II)/ammonia molar ratio can vary from 1/1 to 1/4 approximately. According to a preferred embodiment of the invention, the ammoxidation reaction is carried out using a phase gas in which the alcohol of formula (II)/ammonia molar ratio is equal to 1/3 approximately.

Within the gas phase, the alcohol of formula (II)/oxygen molar ratio can vary from 1/1.5 to 1/5 approximately. According to a preferred embodiment of the invention, the ammoxidation reaction is carried out using a gas phase in which the alcohol of formula (II)/oxygen molar ratio is equal to 1/3.5 approximately.

According to a particularly preferred embodiment of the invention, the ammoxidation reaction is carried out using a gas phase in which the alcohol of formula (II)/oxygen/ammonia molar ratio is 1/3.5/3 approximately.

According to a specific embodiment of the process in accordance with the invention and although this is in no way necessary for the satisfactory progression of the ammoxidation reaction, the catalyst of formula (I) can be supported by a porous solid support. In this case, the porous solid support can be chosen from supports based on silica, in particular in the form of silica gel (CARiACT® type) or of mesostructured silica (such as, for example, the mesostructured silica of SBA-15 type), and also from supports based on mixed silicon oxides, such as, for example, $SiO_2$—$TiO_2$ or $SiO_2$—$ZrO_2$; and supports made of silicon carbide (SiC), and the like.

Such a porous solid support preferably exhibits a mean porosity of between 0.1 cm³/g and 2.0 m³/g inclusive and more preferably still between 0.5 cm³/g and 1.5 cm³/g inclusive.

When the reaction is terminated, the separation of the coproducts of the reaction can be carried out by any appropriate technique known to a person skilled in the art, for example by distillation.

DETAILED DESCRIPTION

The present invention is illustrated by the following implementational examples, to which, however, it is not limited.

EXAMPLES

In the examples which follow, the following starting materials were used:
97% Oxalic acid (Fluka),
Iron nitrate nonahydrate (Sigma Aldrich),
Antimony(III) oxide (Sigma Aldrich),
99% Allyl alcohol (Fluka),
Ammonia (Praxair),
Oxygen (Alphagaz).

Catalysts of formula (I) with x=0.4 to 1 were prepared from these starting materials. The value of y for each of these catalysts is determined in accordance with the electrical neutrality and/or the valences of the elements. It was not measured experimentally.

The synthesis of the acrylonitrile was carried out in the gas phase in a tubular fixed bed reactor with a diameter of 15 mm and a length of 120 mm. The temperature of the reactor was precisely regulated and controlled by a thermocouple.

Example 1

Synthesis of a Catalyst of Formula (I) with x=0.6

A 0.05M solution was prepared by dissolving 2.21 g of oxalic acid in 500 ml of water at 80° C. with stirring. Once dissolution was complete, 140.97 g of iron nitrate nonahydrate were added to the oxalic acid solution while maintaining the temperature at 80° C. After complete dissolution of the iron nitrate nonahydrate, 30.51 g of antimony(III) oxide were added. The resulting solution was left to evaporate while maintaining the temperature at 80° C., with stirring, until a viscous solution was obtained, which was then dried in an oven at 120° C. for 72 hours.

After drying, the product obtained was pressed in the form of pellets which were subsequently ground in order to obtain a pulverulent product comprising particles having a size of between 250 and 630 µm. These particles were then calcined under static air from ambient temperature up to 500° C. while observing a temperature rise gradient of 1° C./min and then a phase of maintenance at 500° C. for 8 hours. The catalyst was subsequently left in the oven until the temperature had returned to 50° C. A catalyst exhibiting an Sb/Fe ratio of 0.6 (i.e., x=0.6) was obtained.

Example 2

Synthesis of a Catalyst of Formula (I) with x=0.8

A catalyst of formula (I) in which x=0.8 was prepared according to a procedure identical to that of Example 1 above but using 2.21 g of oxalic acid, 27.7 g of iron nitrate nonahydrate and 8 g of antimony(III) oxide.

Example 3

Synthesis of a Catalyst of formula (I) with x=0.4

A catalyst of formula (I) in which x=0.4 was prepared according to a procedure identical to that of Example 1 above but using 2.21 g of oxalic acid, 87.3 g of iron nitrate nonahydrate and 12.6 g of antimony(III) oxide.

Example 4

Synthesis of a Catalyst of Formula (I) with x=1.0

A catalyst of formula (I) in which x=1.0 was prepared according to a procedure identical to that of Example 1 above but using 2.21 g of oxalic acid, 22.2 g of iron nitrate nonahydrate and 8.0 g of antimony(III) oxide.

Example 5

Synthesis of Acrylonitrile from Allyl Alcohol 5 g of the catalyst prepared according to Example 1 were placed in a fixed bed reactor. The reaction was carried out with a 7.2% by weight aqueous allyl alcohol solution. The reactor was heated to 400° C. and then fed with reactants (allyl alcohol/O$_2$/NH$_3$) at atmospheric pressure. The contact time of the reactants with the catalyst was of the order of 0.1 s and the reaction time was 5 hours.

The products resulting from the reaction were analysed after trapping at the reactor outlet in a bubbler maintained at low temperature (−4° C.). The liquid obtained was subsequently analysed on a gas chromatograph equipped with a flame ionization detector.

The operating conditions used are summarized in Table I below:

TABLE I

|  | Control (*) | Test 1 | Test 2 | Test 3 | Test 4 |
|---|---|---|---|---|---|
| Allyl alcohol/O$_2$/NH$_3$ molar ratio | 1/1.6/0.4 | 1/1.6/0.4 | 1/3.5/0.8 | 1/3.5/1.5 | 1/3.5/3 |
| Conversion of the allyl alcohol | 14% | 87% | 95% | 99% | 99% |
| % Acrylonitrile | 0 | 17 | 38 | 52 | 63 |
| % Acrolein | 24 | 52 | 43 | 26 | 3 |
| % Acetaldehyde | 16 | 5 | 4 | 1 | 1 |

TABLE I-continued

|  | Control (*) | Test 1 | Test 2 | Test 3 | Test 4 |
|---|---|---|---|---|---|
| % Propionaldehyde | 21 | 5 | 4 | 0 | <1 |
| % Acetonitrile | 0 | 1 | 2 | 2 | 1 |

(*): Catalyst-free process: not in accordance with the invention

These results demonstrate, first of all, that the presence of a catalyst in accordance with the present invention is necessary in order to carry out the ammoxidation reaction of allyl alcohol to give acrylonitrile in the presence of ammonia and oxygen. Furthermore, they show that the presence of a catalyst in accordance with the present invention increases, with identical operating conditions, the conversion of the allyl alcohol (from 14% to 87%) and also increases the selectivity for acrylonitrile and for acrolein, from 0% and 24% to 17% and 52% respectively. In addition, according to a preferred embodiment of the process in accordance with the invention, it is seen that the increase in the NH$_3$/allyl alcohol molar ratio makes it possible to further improve the selectivity for acrylonitrile and also the conversion of the allyl alcohol. Under the optimum implementational conditions of this example, the conversion of the allyl alcohol is 99% with a selectivity for acrylonitrile of 63%.

Example 6

Synthesis of Acrylonitrile from Allyl Alcohol

In this example, the ammoxidation reaction of allyl alcohol was carried out according to the process described in detail in Example 5 above under operating conditions which make possible the complete conversion of the allyl alcohol, using the catalyst prepared according to Example 1, at a temperature of 400 or 450° C., and using different allyl alcohol/NH$_3$ molar ratios.

The reaction time was 5 hours.

As for Example 5, the products resulting from the reaction were analysed after trapping at the reactor outlet in a bubbler maintained at low temperature (−4° C.). The liquid obtained is subsequently analysed on a gas chromatograph equipped with a flame ionization detector.

The operating conditions used are summarized in Tables II and III below:

TABLE II

|  | Test 5 | Test 6 | Test 7 |
|---|---|---|---|
| Reaction temperature | 400° C. | 450° C. | 450° C. |
| Contact time (s) | 0.1 | 0.1 | 0.16 |
| Allyl alcohol/O$_2$/NH$_3$ molar ratio | 1/3.5/2 | 1/3.5/1 | 1/3.5/2 |
| Conversion of the allyl alcohol | 100% | 100% | 100% |
| % Acrylonitrile | 67 | 51 | 76 |
| % Acrolein | 11 | 24 | 9 |
| % Acetaldehyde | 1 | 1 | 1 |
| % Propionaldehyde | 1 | 1 | 1 |
| % Acetonitrile | 4 | 2 | 3 |
| Carbon balance | 97% | 101% | 101% |

TABLE III

|  | Test 8 | Test 9 | Test 10 |
|---|---|---|---|
| Reaction temperature | 450° C. | 400° C. | 400° C. |
| Contact time (s) | 0.1 | 0.16 | 0.16 |

TABLE III-continued

|  | Test 8 | Test 9 | Test 10 |
|---|---|---|---|
| Allyl alcohol/$O_2$/$NH_3$ molar ratio | 1/3.5/3 | 1/3.5/1 | 1/3.5/3 |
| Conversion of the allyl alcohol | 100% | 100% | 100% |
| % Acrylonitrile | 83 | 50 | 76 |
| % Acrolein | 4 | 27 | 1 |
| % Acetaldehyde | <1 | 2 | 1 |
| % Propionaldehyde | 1 | 1 | 1 |
| % Acetonitrile | 3 | 3 | 5 |
| Carbon balance | 92% | 93% | 85% |

These tests show that the best results in terms of selectivity with regard to the formation of acrylonitrile are obtained with Test 8 carried out at 450° C. with a contact time of 0.1 s and an ally alcohol/$NH_3$ molar ratio of 1/3. An acrylonitrile yield of 83% with complete conversion of allyl alcohol is then obtained.

The invention claimed is:

1. A process for the production of a nitrile from an alcohol in the presence of a catalyst, said method comprising:
a stage of ammoxidation of an alcohol of following formula (II):

$$CH_2=C(R^1)-CH_2-OH \quad (II)$$

in which $R^1$ is a hydrogen atom or a methyl radical, to result in a nitrile of following formula (III):

$$CH_2=C(R^1)-C\equiv N \quad (III)$$

in which $R^1$ has the same meaning as in the above formula (II), said reaction being carried out in gas phase, said gas phase comprising at least ammonia and oxygen, and in the presence of a solid catalyst selected from the group consisting of compounds of following formula (I):

$$Sb_xFe_1O_y \quad (I)$$

in which x varies from 0.4 to 1 inclusive and y varies from 1.6 to 4 inclusive.

2. The process according to claim 1, wherein $R^1$ is a hydrogen atom and acrylonitrile is produced.

3. The process according to claim 1, wherein x varies from 0.5 to 0.8 inclusive.

4. The process according to claim 1, wherein x=0.6.

5. The process according to claim 1, wherein the ammoxidation reaction is carried out at a temperature varying from 350 to 450° C.

6. The process according to claim 1, wherein the ratio of the volume of catalyst to the total flow rate by volume of gas injected into the reactor, calculated at the temperature and at the pressure of the reaction, varies from 0.05 to 2 s.

7. The process according to claim 1, wherein, within the gas phase, the alcohol of formula (II)/ammonia molar ratio varies from 1/1 to 1/4.

8. The process according to claim 1, wherein, within the gas phase, the alcohol of formula (II)/oxygen molar ratio varies from 1/1.5 to 1/5.

9. The process according to claim 1, wherein the ammoxidation reaction is carried out using a gas phase in which the alcohol of formula (II)/oxygen/ammonia molar ratio is 1/3.5/3.

10. The process according to claim 1, wherein the catalyst of formula (I) is supported by a porous solid support.

* * * * *